| United States Patent [19] | [11] Patent Number: 4,607,107 |
| Cooper et al. | [45] Date of Patent: * Aug. 19, 1986 |

[54] (4-AMINOALKYL-2-PYRIDYL ALKYL)GUANIDINES

[75] Inventors: David G. Cooper, Letchworth; George S. Sach, Welwyn, both of England

[73] Assignee: Smith Kline & French Laboratories Ltd., Welwyn Garden City, England

[*] Notice: The portion of the term of this patent subsequent to Mar. 4, 2003 has been disclaimed.

[21] Appl. No.: 569,433

[22] Filed: Feb. 17, 1984

Related U.S. Application Data

[62] Division of Ser. No. 467,065, Feb. 16, 1983, Pat. No. 4,439,609, which is a division of Ser. No. 302,941, Sep. 16, 1981, Pat. No. 4,385,058.

[51] Int. Cl.[4] .......................................... C07D 211/70
[52] U.S. Cl. .................................. 546/332; 546/193; 546/281; 546/300
[58] Field of Search ............... 546/193, 281, 332, 300

[56] References Cited

U.S. PATENT DOCUMENTS

| 3,535,328 | 10/1970 | Zielinski | 546/275 |
| 3,968,216 | 7/1976 | Black et al. | 424/263 |
| 4,128,658 | 12/1978 | Price et al. | 424/285 |
| 4,250,316 | 2/1981 | Algieri et al. | 546/287 |
| 4,490,533 | 12/1984 | Bolhofer et al. | 546/332 |

FOREIGN PATENT DOCUMENTS 2030979A  4/1980  United Kingdom .

OTHER PUBLICATIONS

Derwent Abstract 55416E (EP 55,179).

*Primary Examiner*—Joseph Paul Brust
*Attorney, Agent, or Firm*—Joan S. Keps; Stuart R. Suter; Alan D. Lourie

[57] ABSTRACT

This invention relates to 4-aminoalkyl-2-pyridyl alkyl-guanidines which are intermediates for pyrimidone compounds having histamine $H_2$-antagonist activity.

2 Claims, No Drawings

(4-AMINOALKYL-2-PYRIDYL ALKYL)GUANIDINES

This is a division of application Ser. No. 467,065 filed Feb. 16, 1983 now U.S. Pat. No. 4,439,609, which is a division of application Ser. No. 302,941 filed Sept. 16, 1981 now U.S. Pat. No. 4,385,058.

This invention relates to certain pyrimidone derivatives, pharmaceutical compositions containing them and methods of blocking histamine $H_2$-receptors by administering these compounds.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427(1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine $H_1$- and $H_2$-receptors and blockade of both types of receptors is useful. These conditions include inflammation mediated by histamine, for example skin inflammation, and those hypersensitivity responses due to the action of histamine at $H_1$- and $H_2$-receptors, for example allergies.

U.S. Pat. No. 4,154,834 describes inter alia a class of 4-pyrimidone derivatives with a 2-(pyridylalkylamino) or 2-(pyridylalkylthioalkylamino) substituent as histamine $H_1$- and $H_2$-antagonists. One compound specifically referred to (in Example 12(f)) is 2-[2-(2-pyridylmethylthio)ethylamino]-5-(3-pyridylmethyl)-4-pyrimidone. We have found that the histamine $H_2$-antagonist activity of this class of compounds can be increased by introducing a particular type of substituent (a $-CH_2NR^1R^2$ group where $R^1$ and $R^2$ are $C_1$–$C_4$ alkyl or together with the nitrogen atom to which they are attached form a pyrrolidino or piperidino group) into the 4-position of the 2-pyridyl group. It is surprising that the histamine $H_2$-antagonist activity is increased as we have found that the introduction of this particular type of substituent into the 6-position of the 2-pyridyl group in a closely analogous compound reduces histamine $H_2$-antagonist activity.

Accordingly the present invention provides compounds of Structure 1

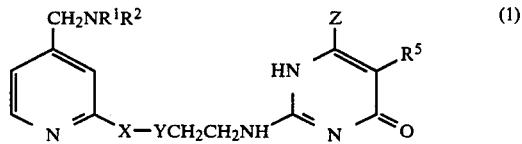

in which $R^1$ and $R^2$ are $C_1$–$C_4$ alkyl or together with the nitrogen atom to which they are attached form a pyrrolidino or piperidino group;

Y is methylene or sulphur;

X is methylene or oxygen provided that X is methylene when Y is sulphur;

Z is hydrogen or $C_1$–$C_4$ alkyl; and $R^5$ is hydrogen, $C_{1-4}$ alkyl or -A-B where
  A is $C_1$–$C_4$ alkylene and
  B is a pyridyl or N-oxopyridyl group optionally substituted by one or more $C_1$–$C_4$ alkyl, $C_1$–$C_4$ alkoxy or hydroxy groups;
  quinolyl, thiazolyl, furanyl, thienyl, naphthyl, 5-(1,3-benzodioxolyl), 6-(2,3-dihydro-1,4-benzodioxinyl);
  a phenyl group optionally substituted by one to three halogen, $C_1$–$C_4$ alkoxy, $C_1$–$C_4$ alkyl or hydroxy groups;
  a 2-furanyl or 2-thienyl group substituted in the 5-position by $-CH_2NR^1R^2$;
  a phenyl group substituted in the 3- or 4-position by $-CH_2NR^1R^2$;
  a 3-pyridyl group substituted in position 5 or 6 by $-CH_2NR^1R^2$;
  a 4-pyridyl group substituted in position 2 by $-CH_2NR^1R^2$; or
  a 2-pyridyl group substituted in position 4 or 5 by $-CH_2NR^1R^2$;

and pharmaceutically acceptable acid addition salts thereof.

The compounds of Structure 1 are shown and described as 4-pyrimidone derivatives and these derivatives exist in equilibrium with the corresponding 6-tautomers. These compounds also exist to a lesser extent as the hydroxy tautomers, and the 2-aminopyrimidone group may also exist in 2-imino tautomeric forms.

In a particular class of compounds of Structure 1 X is methylene and Y is sulphur. A particular meaning for $R^1$ and $R^2$ is methyl. Preferably $R^5$ is -A-B where A is methylene.

Specific meanings for the group B are 3-pyridyl, 6-methyl-3-pyridyl, 5,6-dimethyl-3-pyridyl, 6-methoxy-3-pyridyl, 2-methoxy-4-pyridyl, 6-hydroxy-3-pyridyl, 2-hydroxy-4-pyridyl, N-oxo-3-pyridyl, N-oxo-6-methyl-3-pyridyl, N-oxo-4-pyridyl, 3-quinolyl, 2-thiazolyl, 2-furanyl, 5-dimethylaminomethyl-2-furanyl, 5-dimethylaminomethyl-2-thienyl, 3-(dimethylaminomethyl)phenyl, 4-(dimethylaminomethyl)phenyl, 5-(dimethylaminomethyl)-3-pyridyl, 6-(dimethylaminomethyl)-3-pyridyl, 2-(dimethylaminomethyl)-4-pyridyl, 4-(dimethylaminomethyl)-2-pyridyl and 5-(dimethylaminomethyl)-2-pyridyl.

Specific compounds of Structure 1 are:

(a) 2-[2-(4-dimethylaminomethyl-2-pyridylmethylthio)ethylamino]-5-(6-methyl-3-pyridylmethyl)-4-pyrimidone, (b) 2-[2-(4-dimethylaminomethyl-2-pyridylmethylthio)ethylamino]-5-(3-pyridylmethyl)-4-pyrimidone, (c) 2-[2-(4-dimethylaminomethyl-2-pyridylmethylthio)ethylamino]-5-(2-hydroxy-4-pyridylmethyl)-4-pyrimidone, (d) 2-[4-(4-dimethylaminomethyl-2-pyridyl)butylamino]5-(6-methyl-3-pyridylmethyl)-4-pyrimidone, (e) 2-[2-(4-dimethylaminomethyl-2-pyridylmethylthio)ethylamino]-5-(5,6-dimethyl-3-pyridylmethyl)-4-pyrimidone, and their pharmaceutically acceptable acid addition salts.

The compounds of Structure 1 can be prepared by reacting an amine of Structure 2 (in which $R^1$, $R^2$, X and Y are as defined with reference to Structure 1) with a pyrimidone of Structure 3 (in which Q is nitroamino, lower alkylthio, benzylthio, chlorine, bromine or other group which can be displaced with a primary amine and R has the same significance as $R^5$ or can be a protected derivative of the group -A-B), removing any protecting group present, and optionally converting the product into a pharmaceutically acceptable acid addition salt.

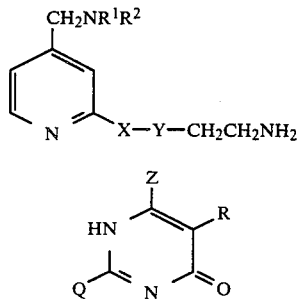

This process can be carried out in the absence of a solvent at an elevated temperature or in the presence of a non-reactive polar solvent. For example, when Q is nitroamino the reaction can be carried out in a lower alkanol (for example ethanol or 2-propanol), pyridine or anisole at the reflux temperature of the reaction mixture, or when Q is methylthio the reaction can be carried out in the absence of solvent at 140°–170° or in refluxing pyridine. Preferably Q is nitroamino.

The compounds of Structure 1 can also be prepared by reacting a guanidine of Structure 4 (in which $R^1$, $R^2$, X and Y are as defined with reference to Structure 1) with a compound of Structure 5 (in which Z and R are as defined with reference to Structure 1 and $R^5$ is lower alkyl).

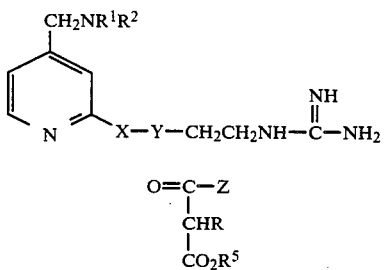

Preferably this reaction is carried out in a $C_1$–$C_4$ alkanol under basic conditions, for example in the presence of a sodium $C_1$–$C_4$ alkoxide in a $C_1$–$C_4$ alkanol.

Compounds of Structure 1 in which X is methylene and Y is sulphur can also be prepared by reacting a compound of Structure 6 (in which L is a group displaceable with a thiol and $R^1$, and $R^2$ are as defined for Structure 1) with a compound of Structure 7

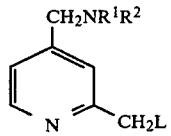

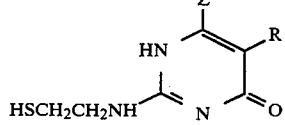

(in which Z is hydrogen or $C_1$–$C_4$ alkyl and R is as defined for Structure 3), removing any protecting group present and optionally converting the product into a pharmaceutically-acceptable acid-addition salt. Examples of groups displaceable with a thiol are chlorine, bromine, hydroxy, alkanoyloxy (e.g. acetoxy), arylsulphonyloxy (e.g. 4-methylbenzenesulphonyloxy), alkylsulphonyloxy (e.g. methanesulphonyloxy) and triarylphosphonium (e.g. triphenylphosphonium). Preferably L is hydroxy and the reaction is carried out under acidic conditions. When L is chlorine or bromine the reaction is preferably carried put in the presence of a strong base e.g. with sodium ethoxide in ethanol.

When L is triarylphosphonium the reaction is preferably carried out under neutral conditions e.g. in a halogenated hydrocarbon, for example chloroform. When L is aryl- or alkylsulphonyloxy the reaction is preferably carried out under mildly basic conditions, e.g. in pyridine solution.

The compounds of Structure 1 in which B is a 6-hydroxy-3-pyridyl or 2-hydroxy-4-pyridyl group can be prepared by dealkylating the corresponding compounds of Structure 1 in which B is a 3- or 4-pyridyl group with a 6- or 2-lower alkoxy or benzyloxy substituent. Preferably this dealkylation is carried out using 1 to 3 N ethanolic hydrochloric or hydrobromic acid at an elevated temperature, for example the boiling point of the mixture.

The compounds of Structure 3 can be prepared as described in U.S. Pat. Nos. 4,145,546 and 4,154,834, European Specification No. 4793 and European Patent application No. 81301324.

The amines of Structure 2, which are novel and form part of this invention, can be prepared by one of the following three methods:

(i) for those compounds in which X is methylene and Y is sulphur; by reacting a pyridyl derivative of Structure 6 (in which L is a group displaceable with a thiol) with cysteamine. Preferably L is chlorine and the reaction is carried out under basic conditions, for example in a lower alkanol in the presence of an alkali metal alkoxide. When L is hydroxy the reaction is preferably carried out under acidic conditions, for example in acetic, hydrobromic or hydrochloric acid.

Compounds of Structure 6 in which L is hydroxy can be prepared by hydroxymethylating a compound of Structure 8, in which

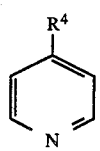   (8)

$R^4$ is —CN or —CN$_2$NR$^1$R$^2$ (and R$^1$ and R$^2$ are as defined for Structure 1), for example using methanol and ammonium persulphate. The products in which R$^4$ is —CN are then reduced, (for example using lithium aluminium hydride) and alkylated (for example when R$^1$ and R$^2$ are lower alkyl by reductive alkylation with hydrogen and an aldehyde). Optionally the products in which L is hydroxy are converted into the corresponding compounds in which L is chlorine or bromine by reaction with a thionyl halide, for example thionyl chloride in dichloromethane.

(ii) for those compounds in which X and Y are both methylene; by reducing a pyridyl derivative of Structure 10, for example with lithium aluminium hydride.

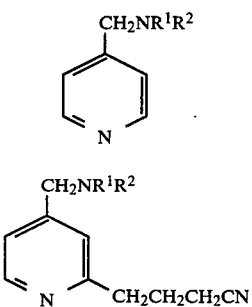

The compounds of Structure 10 can be prepared by reacting a compound of Structure 9 with 4-cyanobutyric acid, ammonium persulphate and silver nitrate.

(iii) for those compounds in which X is oxygen and Y is methylene; by reducing a compound of Structure 11, 12, or 13, for example using lithium aluminium hydride

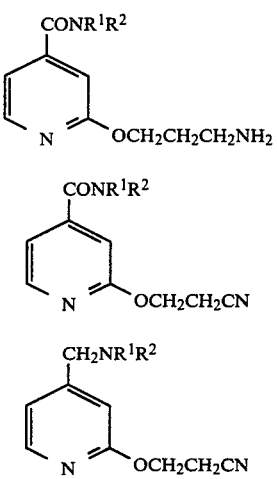

or by reacting a compound of Structure 14 with 3-aminopropanol under basic conditions.

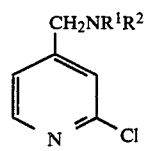   (14)

The compounds of Structure 11, 12, and 13 can be prepared by reacting a compound of Structure 15 or 14 with

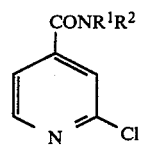   (15)

3-aminopropanol or 3-hydroxypropionitrile under basic conditions. The compounds of Structure 14 can be prepared by successively reacting a compound of Structure 16 with thionyl chloride and an amine R$^1$R$^2$NH.

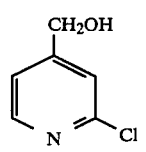   (16)

The guanidines of Structure 4 can be prepared by reacting an amine of Structure 2 with an S-alkyl isothiouronium salt (for example S-methylisothiouronium hemisulphate in water or a C$_1$–C$_4$ alkanol) or with cyanamide at about pH 8 in hot water.

Acid addition salts of compounds of Structure 1 can be formed from the corresponding bases by standard procedures for example by reacting the base with an acid in a lower alkanol or by the use of an ion-exchange resin. Salts of compounds of Structure 1 can be interconverted using an ion-exchange resin. Pharmaceutically acceptable acid addition salts of the compounds of Structure 1 include those formed with hydrochloric, hydrobromic, sulphuric, phosphoric, acetic, citric, maleic, lactic, ascorbic and methanesulphonic acids.

The activity of the compounds of Structure 1 as histamine H$_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. There are actions of histamine which, according to Ash and Schild, Brit. J. Pharmac. Chemother. 27, 247 (1966), are not mediated by histamine H$_1$-receptors.

The histamine H$_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

Inhibition of histamine-stimulated secretion of gastric acid can be measured by using a lumen-perfused stomachs of rats anaesthetised with urethane using the following modification of the method of Ghosh and Schild, Brit. J. Pharmac. Chemother. 13 54 (1958):

Female Sprague-Dawley rats (160–200 g) are starved overnight and anaesthetised with urethane given intraperitoneally in one dose (200 mg). The trachea and jugular veins are both cannulated and a mid-line incision is made in the abdomen exposing the stomach which is cleared from connective tissue. A small incision is made in the rumen of the stomach and the stomach is washed with 5% w/v glucose solution. The oesophagus is partially cleared of connective tissue and cannulated with polythene tubing and the oesophagus and vagi are then cut above the cannula. An incision is made in the antrum and a cannula is passed into the stomach via the ruminal incision and through into the antrum so that the head of the cannula lies in the body of the stomach. A funnel-shaped cannula is inserted in the ruminal incision and tied into position so that the line between the rumen and the body coincides with the edge of the funnel. The antral cannula is tied into place to reduce the possibility that antrally released gastrin will effect gastric acid secretion. Two stab wounds are made in the abdominal wall, and the stomach cannulae passed through. The stomach is perfused through the oesophageal and stomach cannulae with 5.4% w/v glucose solution at 37° at 1–2 ml min$^{-1}$. The effluent is passed over a micro-flow pH electrode and recorded by a pH meter fed to an anti-log unit and flat-bed recorder. The basal output of acid secretion from the stomach is monitored by measurement of the pH of the perfusion effluent. A sub-maximal dose of histamine is continuously infused into the jugular vein and produces a stable plateau of acid secretion and the pH of the perfusion effluent is determined when this condition is obtained. Infusion of histamine at a rate of 0.25 micromol kg$^{-1}$ min$^{-1}$ produces 70% of maximum histamine stimulated gastric acid secretion. The test compound is then administered intravenously into the second jugular vein and washed in with glucose solution (0.2 ml, 5.4% w/v). The difference in acid secretion between basal output and the histamine stimulated plateau level and the reduction of acid secretion caused by the test compound are calculated from the difference in pH of the perfusion effluent. ED$_{50}$ values (for inhibiting sub-maximal acid secretion by 50%) are determined by administering one dose of test compound to one rat and repeating this in at least four rats for each of three or more dose levels. The results obtained are then used to calculate the ED$_{50}$ value by the standard method of least squares.

Heidenhain pouch dogs can be prepared and used as described in European Specification No. 15138.

In the guinea pig atrium test a spontaneously beating isolated portion of the guinea pig right atrium is secured under tension (300 mg) between an anchorage and a transducer in a 15 ml tissue bath and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity (pA$_2$ value).

To illustrate the level of activity of the compounds of the invention we have determined that the products of Examples 1 to 4 have ED$_{50}$ values in the lumen-perfused rat test of less than 0.1 micromol kg$^{-1}$ i.v. and pA$_2$ values in the guinea pig atrium test of more than 7.0. The product of Example 1 also showed a longer duration of activity than cimetidine after intravenous administration in the Heidenhain pouch dog when dose levels had been adjusted to produce similar peak responses.

Compounds of Structure 1 and their pharmaceutically acceptable acid addition salts can be administered orally, parenterally, topically or rectally. They will normally be administered as a pharmaceutical composition.

The invention also provides pharmaceutical compositions comprising a compound of Structure 1 or a pharmaceutically acceptable acid addition salt thereof and pharmaceutically acceptable carrier. The pharmaceutical compositions can also comprise an accepted drug in addition to a compound of Structure 1, for example a histamine H$_1$-antagonist, e.g. mepyramine.

The pharmaceutical carrier employed can be a solid or liquid. Examples of solid carriers or lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

For oral administration if a solid carrier is used, the composition can be prepared in the form of a tablet, capsule containing powder or pellets, troche or lozenge. The amount of solid carrier in a unit dosage form will generally be from about 25 mg to about 300 mg. If a liquid carrier is used, the composition can be in the form of a syrup, emulsion, multiple emulsion, sterile injectable liquid or an aqueous or non-aqueous solution or liquid suspension. Other additives such as preservatives, for example antioxidants or antibacterials, and/or flavouring or colouring agents can also be included. The sterile injectable liquids can be prepared in ampoules, multidose vials or unit dose disposable systems. For topical application the preparation can be in a semi-solid form, for example a cream, paste, ointment or gel, in a liquid or aerosol form. The composition can also be a suppository formulation. The pharmaceutical compositions are prepared by conventional techniques involving procedures such as milling, mixing, granulating and compressing, spray drying, freeze drying or dissolving or dispersing the ingredients as appropriate to the desired preparation.

The active ingredient is present in the compositions in an effective amount to block histamine H$_2$-receptors involved in the condition being treated. Preferably an oral dosage unit for the inhibition of gastric acid secretion contains 15 to 250 mg of a compound of Structure 1 or a pharmaceutically acceptable acid addition salt thereof (calculated as the free base).

This invention also provides a method of blocking histamine H$_2$-receptors which comprises administering to an animal an effective amount to block said receptors of a compound of Structure 1 or a pharmaceutically acceptable acid addition salt thereof.

The pharmaceutical compositions of the invention will normally be administered to man for the treatment of gastric and duodenal ulcers and other conditions caused or exacerbated by gastric acidity in the same general manner as that employed for known histamine H$_2$-antagonists, due allowance being made in terms of dose levels for the potency of the compound of the present invention relative to known histamine H$_2$-antagonist drugs. The dosage regimen for an adult patient is an oral dose of 15 to 1500 mg (preferably 20 to 250 mg) or an intravenous, subcutaneous or intramuscular dose of 1.5 to 150 mg (preferably 5 to 20 mg) of compound of Structure 1 or pharmaceutically acceptable acid addition salt thereof calculated as the free base, the composition being administered 1 to 6 times per day.

The dosage regimen for conditions other than acid secretion which are mediated through histamine H$_2$-receptors will be chosen appropriate to the condition, the route of administration and the relative potency of the compounds.

The invention is illustrated by the following Preparations and Examples. Temperatures are given in degrees Centigrade.

PREPARATION 1

(a) A mixture of 4-cyanopyridine (31.2 g), ammonium persulphate (136.8 g), methanol (450 ml), concentrated sulphuric acid (16.2 ml) and water (210 ml) was heated under reflux for 24 hours, and the methanol was removed by distillation. Crushed ice (450 g) was added and the mixture was adjusted to pH 12 with 10M sodium hydroxide and extracted with chloroform. The chloroform extracts were combined and evaporated and the residue was purified by elution from a silica gel column with methanol-chloroform (7.5% v/v) to give 4-cyano-2-hydroxymethylpyridine (18.5 g, 46%) m.p. 92°–94°.

(b) A solution of 4-cyano-2-hydroxymethylpyridine (0.5 g) in tetrahydrofuran (25 ml) was added dropwise over 20 minutes to a stirred mixture of lithium aluminium hydride (0.25 g) in tetrahydrofuran (30 ml) and the mixture was stirred at room temperature for 2 hours. Wet tetrahydrofuran followed by 0.35 ml of 16% w/w aqueous sodium hydroxide and water were added and the mixture was filtered. The filtrate was evaporated to give crude 4-aminomethyl-2-hydroxymethylpyridine (0.28 g).

NMR (CDCl$_3$): p.p.m., assignment, multiplicity, integral; 3.87, C̲H$_2$NH$_2$, s, 1.7; 4.61, C̲H$_2$OH, s, 2; 7.11, 5-pyridyl proton, d of d,1; 7.30, 3-pyridyl proton, d, 1; 8.4, 6-pyridyl proton, d, 1.

(c) A solution of 4-aminomethyl-2-hydroxymethylpyridine (1.38 g) in aqueous formaldehyde (25% w/w, 12 ml) was hydrogenated at 344 kPa and 30° for 23 hours with 10% palladium on charcoal catalyst. The mixture was filtered and the filtrate was extracted with chloroform. The chloroform phase was extracted with water at pH 5 and this aqueous extract was adjusted to pH 12 and extracted with chloroform. This chloroform extract was evaporated to give 4-dimethylaminomethyl-2-hydroxymethylpyridine (0.47 g) as an oil.

NMR (CDCl$_3$): p.p.m., assignment, multiplicity, integral; 2.26, N(CH$_3$)$_2$, s, 5.5; 3.42, C̲H$_2$N(CH$_3$)$_2$, s, 2; 3.75, OH, broad, 1.3; 4.78, C̲H$_2$OH, s, 2; 7.19+7.28, 5+3 pyridyl protons, d of d+d, 2.1; 8.49, 6-pyridyl proton, d, 1.

PREPARATION 2

Ammonium persulphate (102.7 g) in water (200 ml) was added over 40 minutes to a refluxing solution of 4-dimethylaminomethylpyridine (40.86 g), methanol (450 ml), water (210 ml) and concentrated sulphuric acid (30 ml). The resulting solution was refluxed for 2 hours, water (300 ml) was added and the methanol was distilled off. The cooled solution was basified and extracted with chloroform to give 4-dimethylaminomethyl-2-hydroxymethylpyridine (19.65 g) b.p. 92°–120°/0.06 mm Hg.

PREPARATION 3

4-Dimethylaminomethyl-2-hydroxymethylpyridine (13.45 g) in dichloromethane (200 ml) was added dropwise to a stirred solution of thionyl chloride (30 ml) in dichoromethane (150 ml). The resulting red mixture was stirred for 1 hour then concentrated in vacuo. The residue was treated with ether (300 ml) to yield a crystalline solid. Recrystallisation from methanol/ether (1:3) yielded 2-chloromethyl-4-dimethylaminomethylpyridine dihydrochloride (20.04 g) as an orange solid m.p. 202°–204°.

PREPARATION 4

Cysteamine hydrochloride (3.75 g) was added to a stirred solution of sodium ethoxide (prepared from 2.83 g sodium) in ethanol (200 ml) and the mixture was cooled to less than 10°. 2-Chloromethyl-4-dimethylaminomethylpyridine dihydrochloride (7.3 g) was added portionwise and the solution was stirred for 1 hour. Water (200 ml) was added, the pH was adjusted to ca. 4 with hydrochloric acid and the volume was reduced to ca. 100 ml. The solution was extracted with chloroform, the aqueous phase was basified to pH 12 and extracted with chloroform to give 2-[4-dimethylaminomethyl-2-pyridylmethylthio)ethylamine (4.7 g) as an oil.

NMR(CDCl$_3$) p.p.m., assignment, multiplicity, integral: 1.51, NH$_2$, s, 2.2; 2.28, N(CH$_3$)$_2$, s, 6; 2.65+2.85; SC̲H$_2$C̲H$_2$NH$_2$, mx2, 4.2; 3.46, CH$_2$SC̲H$_2$CH$_2$NH$_2$, s, 2.1; 3.86, C̲H$_2$N(CH$_3$)$_2$, s, 2.1; 7.17, 5-pyridyl proton, d of d, 1; 7.36, 3-pyridyl proton, d, 1.1; 8.49, 6-pyridyl proton, d, 1.1.

PREPARATION 5

(a) Ammonium persulphate (54.8 g) in water (150 ml) and 4-cyanobutyric acid (68 g) in water (300 ml) were added separately and simultaneously over 30 minutes to a mixture of 4-dimethylaminomethylpyridine (16.32 g), silver nitrate (4 g), water (200 ml) and concentrated sulphuric acid (25 ml) stirred at 80°. The reaction mixture was stirred at 80° for 1.5 hours, cooled, poured onto crushed ice (400 g) and aqueous ammonia (28% w/w, 200 ml). The solution was extracted with chloroform (900 ml) and the chloroform extracts were washed with dilute sodium hydroxide, dried over magnesium sulphate, and concentrated in vacuo to give 2-(3-cyanopropyl)-4-dimethylaminomethylpyridine (9 g) as a clear oil b.p. 110°–112°/0.1 mm Hg.

NMR (CDCl$_3$): p.p.m., assignment, multiplicity, integral; 2.15+2.23+2.40, C̲H$_2$C̲H$_2$C̲H$_2$CN+N(CH$_3$)$_2$+CH$_2$CH$_2$C̲H$_2$CN, m+s+m, 10; 2.92; C̲HCH$_2$CH$_2$CN, t, 2; 3.41, CH$_2$N(CH$_3$)$_2$, s, 2; 7.1, 5+3 pyridyl protons, m, 2; 8.46, 6-pyridyl proton, d, 1.

(b) 2-(3-Cyanopropyl)-4-dimethylaminomethylpyridine (1 g) in diethyl ether (15 ml) was added dropwise to a rapidly stirred suspension of lithium aluminium hydride (0.76 g) in ether (45 ml). The solution was stirred for 2.5 hours. Wet tetrahydrofuran, followed by 16% sodium hydroxide (1 ml) and then water was added and the mixture was filtered. The filtrate was evaporated to give 4-(4-dimethylaminomethyl-2-pyridyl)butylamine (1.02 g) as a clear oil.

NMR (CDCl$_3$): p.p.m., assignment, multiplicity, integral; 1.64+1.70, NH$_2$+CH$_2$(CH$_2$)$_2$CH$_2$NH$_2$, s+m, 6.3; 2.23, N(CH$_3$)$_2$, s, 6; ca 2.75, CH$_2$(CH$_2$)$_2$CH$_2$NH$_2$, m, 3.9; 3.39, CH$_2$N(CH$_3$)$_2$, s, 2; 7.1, 5+3 pyridyl protons, m, 2; 8.46, 6-pyridyl proton, d, 1.

EXAMPLE 1

A solution of 2-(4-dimethylaminomethyl-2-pyridylmethylthio)ethylamine (0.5 g) and 2-nitroamino-5-(6-methyl-3-pyridylmethyl)-4-pyrimidone (0.7 g) in pyridine (3 ml) was heated under reflux for 3.5 hours and evaporated to dryness. The residue was purified by elution from a column of silica gel with ethyl acetate:ethanol: 28% w/w aqueous ammonia (by volume 10:15:2) and recrytallisation from acetonitrile to give 2-[2-(4-dimethylaminomethyl-2-pyridylmethylthio)ethylamino]-5-(6-methyl-3-pyridylmethyl)-4-pyrimidone (0.58 g) m.p. 128°–129.5°.

EXAMPLE 2

A mixture of 4-(4-dimethylaminomethyl-2-pyridyl)butylamine (1 g) and 2-nitroamino-5-(6-methyl-3-pyridylmethyl)-4-pyrimidone (1.26 g) in pyridine (5 ml) was refluxed for 4.5 hours. The solvent was removed in vacuo, the residue chromatographed and then crystallised from ethanol:ether (1:10) to yield 2-[4(4-dimethylaminomethyl-2-pyridyl)butylamino]-5-(6-methyl-3-pyridylmethyl)-4-pyrimidone (0.86 g) m.p. 135°–137°.

C$_{23}$H$_{30}$N$_6$O requires C, 67.95; H, 7.44; N, 20.67; found C, 67.73; H, 7.34; N, 20.47%;

EXAMPLE 3

A solution of 2-(4-dimethylaminomethyl-2-pyridylmethylthio)ethylamine (1 g) and 2-nitroamino-5-(2-methoxy-4-pyridylmethyl)-4-pyrimidone (1.23 g) was refluxed in pyridine (6 ml) for 10 hours, concentrated in vacuo and chromatographed on silica gel column eluted with ethyl acetate-ethanol-28% W:W aqueous ammonia (by volume 10:15:2). Recrystallisation from acetonitrile:ether (1:5) gave 2-[2-(4-dimethylaminomethyl-2-pyridylmethylthio)ethylamino-5-(2-methoxy-4-pyridylmethyl)-4-pyrimidone (1.21 g) m.p. 65°–74° C.

C$_{22}$H$_{28}$N$_6$O$_2$S, 0.56 H$_2$O requires C, 56.62; H, 6.72, N, 18.0; S, 6.87; Found C, 56.42; H, 6.71; N, 17.99; S, 6.68%.

EXAMPLE 4

A mixture of 2-(4-dimethylaminomethyl-2-pyridylmethylthio)ethylamine (1 g) and 2-nitroamino-5-(5,6-dimethyl-3-pyridylmethyl)-4-pyrimidone (1.11 g) in pyridine (3 ml) was heated under reflux for 5 hours and evaporated to dryness in vacuo. The residue was purified by chromatography on silica gel eluted with 20% methanol/chloroform followed by recrystallisation from acetonitrile/water 1:1 to give 2-[2-(4-dimethylaminomethyl-2-pyridylmethylthio)ethylamino]-5-(5,6-dimethyl-3-pyridylmethyl)-4-pyrimidone (0.72 g) m.p. 72°–78°.

C$_{23}$H$_{30}$N$_6$OS. 0.9H$_2$O requires C, 60.78; H, 7.0; N, 18.49; S, 7.06%; Found C, 60.74, H, 6.87, N, 18.35; S, 6.90%.

EXAMPLE 5

The product from Example 3, 2-[2-(4-dimethylaminomethyl-2-pyridylmethylthio)ethylamino]-5-(2-methoxy-4-pyridylmethyl)-4-pyrimidone was heated under reflux in 2N hydrogen chloride in ethanol to give 2-[2-(4-dimethylaminomethyl-2-pyridylmethylthio)ethylamino]-5-(2-hydroxy-4-pyridylmethyl)-4-pyrimidone tetrahydrochloride.

EXAMPLE 6

2-Chloro-4-diethylcarbamoylpyridine is reacted with 3-aminopropanol and sodium hydride to give 3-(4-diethylcarbamoyl-2-pyridyloxy)propylamine, which is reduced with lithium aluminium hydride in tetrahydrofuran to give 3-(4-diethylaminomethyl-2-pyridyloxy)propylamine; this product is heated under reflux in pyridine with 2-nitroamino-5-(6-methyl-3-pyridylmethyl)-4-pyrimidone to give 2-[3-(4-diethylaminomethyl-2-pyridyloxy)propylamino]-5-(6-methyl-3-pyridylmethyl)-4-pyrimidone.

EXAMPLE 7

Reaction of 2-(4-dimethylaminomethyl-2-pyridylmethylthio)ethylamine with 2-nitroamino-5-[5-(1,3-benzodioxolylmethyl]-4-pyrimidone in refluxing pyridine for 10 hours gives 2-[2-(4-dimethylaminomethyl-2-pyridylmethylthio)ethylamino]-5-[5-(1,3-benzodioxolyl)methyl-4-pyrimidone.

EXAMPLE 8

Fusion of 2-(4-dimethylaminomethyl-2-pyridylmethylthio)ethylamine with 2-methylthio-4-pyrimidone and 2-methylthio-5-methyl-4-pyrimidone at 150° for 4 hours gives 2-[2-(4-dimethylaminomethyl-2-pyridylmethylthio)ethylamino]-4-pyrimidone and 2-[2-(4-dimethylaminomethyl-2-pyridylmethylthio)ethylamino]-5-methyl-4-pyrimidone.

EXAMPLE 9

(a) An aqueous mixture of 2-(4-dimethylaminomethyl-2-pyridylmethylthio)ethylamine and S-methyl isothiouronium hemisulphate is heated under reflux to give N-[2-(4-dimethylaminomethyl-2-pyridylmethylthio)ethyl]guanidine hemisulphate.

(b) Reaction of N-[2-(4-dimethylaminomethyl-2-pyridylmethylthio)ethyl]guanidine hemisulphate with ethyl 2-formyl-3-(6-methyl-3-pyridylmethyl)propionate and sodium ethoxide in ethanol gives 2-[2-(4-dimethylaminomethyl-2-pyridyl-methylthio)ethylamino]-5-(6-methyl-3-pyridylmethyl)-4-pyrimidone.

EXAMPLE 10

Fusion of 2-(4-dimethylaminomethyl-2-pyridylmethylthio)ethylamine at 140°–150° with
(a) 2-methylthio-5-(2-pyridylmethyl)-4-pyrimidone
(b) 2-methylthio-5-(3-pyridylmethyl)-4-pyrimidone
(c) 2-methylthio-5-(4-pyridylmethyl)-4-pyrimidone
gives
(a) 2-[2-(4-dimethylaminomethyl-2-pyridylmethylthio)ethylamino]-5-(2-pyridylmethyl)-4-pyrimidone
(b) 2-[2-(4-dimethylaminomethyl-2-pyridylmethylthio)ethylamino]-5-(3-pyridylmethyl)-4-pyrimidone (c) 2-[2-(4-dimethylaminomethyl-2-pyridylmethylthio)ethylamino]-5-(4-pyridylmethyl)-4-pyrimidone

EXAMPLE 11

Reaction of 2-(4-dimethylaminomethyl-2-pyridylmethylthio)ethylamine with
(a) 2-nitroamino-5-(5-dimethylaminomethyl-2-furanylmethyl)-4-pyrimidone
(b) 2-nitroamino-5-(5-dimethylaminomethyl-2-thienylmethyl)-4-pyrimidone
(c) 2-nitroamino-5-(4-dimethylaminomethylbenzyl)-4-pyrimidone
(d) 2-nitroamino-5-(6-dimethylaminomethyl-3-pyridylmethyl)-4-pyrimidone in refluxing ethanol gives
(a) 2-[2-(4-dimethylaminomethyl-2-pyridylmethylthio)ethylamino]-5-(5-dimethylaminomethyl-2-furanylmethyl)-4-pyrimidone
(b) 2-[2-(4-dimethylaminomethyl-2-pyridylmethylthio)ethylamino]-5-(5-dimethylaminomethyl-2-thienylmethyl)-4-pyrimidone
(c) 2-[2-(4-dimethylaminomethyl-2-pyridylmethylthio)ethylamino]-5-(4-dimethylaminomethylbenzyl)-4-pyrimidone
(d) 2-[2-(4-dimethylaminomethyl-2-pyridylmethylthio)ethylamino]-5-(6-dimethylaminomethyl-3-pyridylmethyl)-4-pyrimidone

EXAMPLE 12

(i) Reaction of 4-(hydroxymethyl)pyridine with thionyl chloride gives 4-(chloromethyl)pyridine which is reacted with
(a) dibutylamine
(b) pyrrolidine
(c) piperidine
to give
(a) 4-(dibutylaminomethyl)pyridine
(b) 4-(pyrrolidinomethyl)pyridine
(c) 4-piperidinomethyl)pyridine
which are subjected to the procedures of Preparations 2 to 4 to give
(a) 2-[4-(dibutylaminomethyl)-2-pyridylmethylthio]ethylamine
(b) 2-[4-(pyrrolidinomethyl)-2-pyridylmethylthio]ethylamine
(c) 2-[4-(piperidinomethyl)-2-pyridylmethylthio]ethylamine (ii) Substitution of the preceeding amines for 2-(4-dimethylaminomethyl-2-pyridylmethylthio)ethylamine in the general procedure of Example 1 gives:
(a) 2-[2-(4-(dibutylaminomethyl)-2-pyridylmethylthio)ethylamino]-5-(6-methyl-3-pyridylmethyl)-4-pyrimidone
(b) 2-[2-(4-(pyrrolidinomethyl)-2-pyridylmethylthio)ethylamino]-5-(6-methyl-3-pyridylmethyl)-4-pyrimidone (c) 2-[2-(4-(piperidinomethyl)-2-pyridylmethylthio)ethylamino]-5-(6-methyl-3-pyridylmethyl)-4-pyrimidone

PHARMACEUTICAL COMPOSITIONS

A pharmaceutical composition for oral administration is prepared containing

| | | % by weight |
|---|---|---|
| A | 2-[2-(4-dimethylaminomethyl-2-pyridyl methylthio)ethylamino]-5-(6-methyl-3-pyridylmethyl)-4-pyrimidone | 55 |
| | Dibasic calcium phosphate dihydrate | 20 |
| | Approved coloring agent | 0.5 |
| | Polyvinylpyrrolidone | 4.0 |
| B | Microcrystalline Cellulose | 8.0 |
| | Maize Starch | 8.0 |
| | Sodium glycollate | 4.0 |
| | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients to the dried granules and compressing the mixture into tablets containing 100 mg, 150 mg or 200 mg of the free base.

Other compounds of the invention, for example those specifically described in Examples 2 to 5 can be formulated into pharmaceutical compositions by a similar procedure.

A pharmaceutical composition for injectable administration is prepared by converting 2-[2-(4-dimethylaminomethyl-2-pyridylmethylthio)ethylamino]-5-(6-methyl-3-pyridylmethyl)-4-pyrimidone into the tetrahydrochloride salt form and dissolving this in sterile water to give a 1 to 5% w/w solution. The solution is clarified by filtration and filled into vials which are sealed and sterilised. A suitable vial contains 2 ml of the solution.

What is claimed is:

1. A compound of the formula:

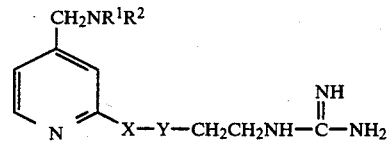

in which
$R^1$ and $R^2$ are $C_1$–$C_4$ alkyl or together with the nitrogen atom to which they are attached form a pyrrolidino or piperidino group;
Y is methylene or sulphur; and
X is methylene or oxygen provided that X is methylene when Y is sulphur.

2. N-[2-(4-Dimethylaminomethyl-2-pyridylmethylthio)ethyl]guanidine hemisulphate.

* * * * *